US006991696B2

(12) United States Patent
Wagner et al.

(10) Patent No.: US 6,991,696 B2
(45) Date of Patent: Jan. 31, 2006

(54) METHOD OF FORMING A DISPOSABLE, REFASTENABLE ABSORBENT ARTICLE

(75) Inventors: Kenneth John Wagner, Greenville, WI (US); Joseph Andrew Mlinar, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 464 days.

(21) Appl. No.: 10/394,361

(22) Filed: Mar. 21, 2003

(65) Prior Publication Data
US 2004/0182502 A1    Sep. 23, 2004

(51) Int. Cl.
*A61F 13/15* (2006.01)
*B32B 31/00* (2006.01)

(52) U.S. Cl. .................. 156/250; 156/66; 156/166; 156/176; 156/182; 156/251; 156/252; 604/358; 604/385.01

(58) Field of Classification Search .................. 156/66, 156/166, 176, 177, 178, 179, 180, 181, 182, 156/250, 251, 252, 253, 254; 604/358, 385.01, 604/393, 394
See application file for complete search history.

(56) References Cited

U.S. PATENT DOCUMENTS

| | | |
|---|---|---|
| 1,467,481 A | 1/1923 | Juline |
| 1,695,109 A | 12/1928 | Kosloff |
| 2,055,973 A | 9/1936 | Goss |
| 2,102,359 A | 12/1937 | Frieman |
| 2,278,029 A | 3/1942 | Walsh et al. |
| 2,322,170 A | 6/1943 | Snyder |
| 2,834,347 A | 5/1958 | Connally |
| 3,008,366 A | 11/1961 | Taylor, Jr. |
| 3,056,323 A | 10/1962 | Kwitek |
| 3,075,684 A | 1/1963 | Rothmann |
| 3,561,332 A | 2/1971 | Ross |
| 3,570,337 A | 3/1971 | Morgan |
| 3,762,542 A | 10/1973 | Grimes |
| 3,800,796 A | 4/1974 | Jacob |
| 3,823,623 A | 7/1974 | Currie et al. |
| 3,826,165 A | 7/1974 | Currie et al. |
| 3,860,003 A | 1/1975 | Buell |
| RE28,911 E | 7/1976 | Jespersen et al. |
| 4,205,679 A | 6/1980 | Repke et al. |
| 4,426,897 A | 1/1984 | Littleton |
| 4,610,189 A | 9/1986 | Lombardo |
| 4,610,680 A | 9/1986 | LaFleur |
| 4,625,612 A | 12/1986 | Oliver |
| 4,639,949 A | 2/1987 | Ales et al. |

(Continued)

FOREIGN PATENT DOCUMENTS

CA    2018028    * 12/1991

(Continued)

*Primary Examiner*—Jeff H. Aftergut
*Assistant Examiner*—Justin Fischer
(74) *Attorney, Agent, or Firm*—Thomas J. Connelly

(57) ABSTRACT

A method of forming a disposable, refastenable absorbent article is disclosed. The method includes directing a first material parallel to and spaced apart from a second material. A pair of lines of perforations is formed across the width of the first material. A pair of attachment members is then secured to the first material such that each bridges across one of the pair of lines of perforations. An absorbent assembly is secured across the first and second materials to form a subassembly. The subassembly is then folded and the first and second materials are bonded together by first and second seam lines. The first and second materials are then separated at locations outward from each of the first and second seam lines to form a disposable, refastenable absorbent article.

20 Claims, 3 Drawing Sheets

U.S. PATENT DOCUMENTS

| | | |
|---|---|---|
| 4,736,660 A | 4/1988 | Benach et al. |
| 4,745,835 A | 5/1988 | Schnitzer |
| 4,769,023 A | 9/1988 | Goebel et al. |
| 4,850,988 A | 7/1989 | Aledo et al. |
| 4,850,992 A | 7/1989 | Amaral et al. |
| 4,940,464 A | 7/1990 | Van Gompel et al. |
| 5,074,854 A | 12/1991 | Davis |
| 5,137,525 A | 8/1992 | Glassman |
| 5,215,275 A | 6/1993 | Gold |
| 5,236,430 A | 8/1993 | Bridges |
| 5,246,433 A | 9/1993 | Hasse et al. |
| 5,370,634 A | 12/1994 | Ando et al. |
| 5,624,420 A | 4/1997 | Bridges et al. |
| 5,836,228 A | 11/1998 | Guthrie et al. |
| 6,036,805 A | 3/2000 | Mcnichols |
| 6,315,022 B1 * | 11/2001 | Herrin et al. ............... 156/459 |
| 6,401,586 B1 | 6/2002 | Wood |
| 6,524,293 B1 | 2/2003 | Elsberg et al. |
| 6,752,796 B2 | 6/2004 | Karami |
| 6,849,067 B2 | 2/2005 | Fletcher et al. |
| 2002/0045879 A1 | 4/2002 | Karami |
| 2002/0148557 A1 | 10/2002 | Heller et al. |
| 2003/0000357 A1 | 1/2003 | Tanaka |
| 2003/0055389 A1 | 3/2003 | Sanders et al. |
| 2003/0135192 A1 | 7/2003 | Guralski et al. |

FOREIGN PATENT DOCUMENTS

| | | | |
|---|---|---|---|
| DE | 3244599 | * | 6/1983 |
| DE | 197 46 456 A1 | | 4/1999 |
| EP | 0 820 843 B1 | | 1/2003 |
| GB | 2 267 024 A | | 11/1993 |
| JP | 2-140163 | * | 5/1990 |
| JP | 3-176053 | * | 7/1991 |
| JP | 4-22359 | * | 1/1992 |
| WO | WO 97/23398 A1 | | 7/1997 |
| WO | WO 02/069867 A1 | | 9/2002 |
| WO | WO 03/024372 A2 | | 3/2003 |
| WO | WO 03/028604 A1 | | 4/2003 |

* cited by examiner

METHOD OF FORMING A DISPOSABLE, REFASTENABLE ABSORBENT ARTICLE

BACKGROUND OF THE INVENTION

Disposable, refastenable absorbent articles for absorbing human discharges can appear similar in size and shape to regular cloth underwear which is designed to be laundered and reused two or more times. A disposable, refastenable absorbent article is an article intended to be worn by persons, such as infants, toddlers, or adults, which is designed for single use or temporary use and is meant to be disposed of after being used once instead of being laundered or dry cleaned for re-use. Some examples of disposable, refastenable absorbent articles include infant diapers, training pants, adult incontinence garments, feminine menstrual pants, etc.

Some disposable, refastenable absorbent articles manufactured today resemble regular cloth underwear in that they have a waist opening and a pair of leg openings. Such disposable, refastenable absorbent articles can be pulled up around the torso of a user in a similar fashion as regular cloth underwear. Still other disposable, refastenable absorbent articles contain an attachment mechanism that will allow the article to be opened into a flat configuration prior to being placed around the torso of a user. This design is beneficial for bed bound users who may be immobile and who need assistance in securing the article in place. Still other disposable, refastenable absorbent articles contain attachment means for opening and closing the waist opening after the article has been positioned around the torso of a user. This feature is advantageous in that the user does not have to undress when there is a desire to check the status of the absorbent article. One such refastenable absorbent article uses a pair of straight perforation lines that extend from the waist opening to the pair of leg openings. The straight perforation lines are designed to be broken either prior to positioning the absorbent article around the user's torso or while the absorbent article is already positioned about the user's torso. The pair of attachment members is then utilized to refasten the absorbent article so that it is snug about the user's torso. This present design suffers from two deficiencies. Namely, a majority of each line of perforations is visually hidden by the attachment members and some users cannot see them and thereby may not even know that they are present. Second, each line of perforations may be ergonomically hard to tear open by older adults, some of who may be suffering from arthritis, because the straight perforation lines are aligned adjacent and parallel to the side seams.

Now a method of forming a disposable, refastenable absorbent article has been invented that uses a pair of lines of perforations that are aligned non-parallel to the side seams to make them more visually noticeable. The configuration of the pair of lines of perforations also enable the user to easily grasp the waist band on either side of each line of perforations and tear them open. The disposable, refastenable absorbent article also possesses an aesthetically pleasing design with improved fit around the human torso.

SUMMARY OF THE INVENTION

Briefly, this invention relates to a method of forming a disposable, refastenable absorbent article. The method includes the steps-of directing a first material parallel to and spaced apart from a second material. The first material has a predetermined width. A pair of lines of perforations is formed across the width of the first material. A pair of attachment members is then secured to the first material such that each attachment member bridges across one of the lines of perforations. One end of each of the pair of attachment members is removeably attached to the first material. An absorbent assembly is secured across the first and second materials to form a subassembly having a transverse centerline. The subassembly is then folded on the transverse centerline and the first and second materials are bonded together by first and second seam lines. Each of the first and second seam lines is aligned non-parallel to and situated outward from one of the lines of perforations to form a waist opening and a pair of leg openings. The first and second materials are then separated at locations outward from each of the first and second seam lines to form a disposable, refastenable absorbent article.

DETAILED DESCRIPTION

Figure 1:
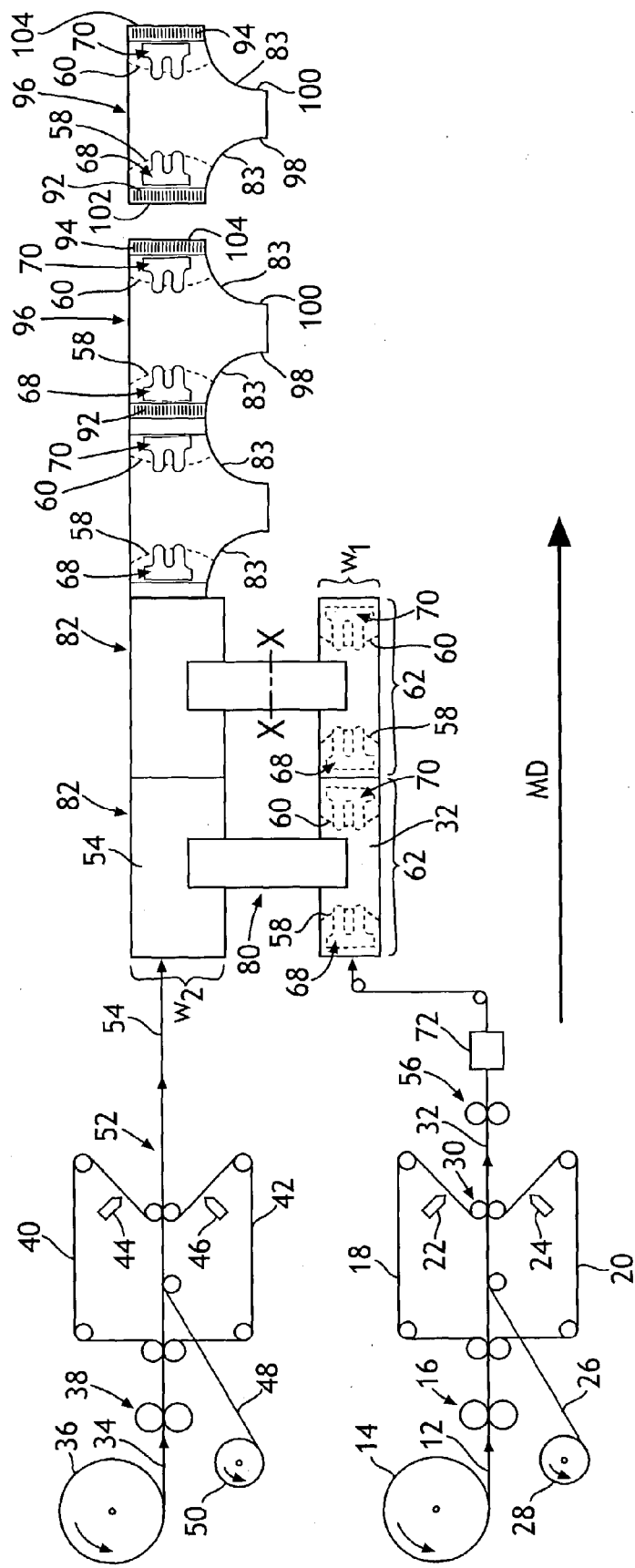
FIG. 1 is a schematic depicting a method of forming a disposable, refastenable absorbent article.

Referring to FIG. 1, a schematic is shown depicting a method of forming a disposable, refastenable absorbent article 10. The term "disposable absorbent article" is used herein to define an article that is intended to be worn by persons, including infants, toddlers or adults, which is designed for single use or temporary use and is meant to be disposed of after being used once instead of being laundered or dry cleaned for re-use. The absorbent article 10 is designed to absorb and/or retain one or more bodily discharges of waste material such as urine, perspiration, excrement, feces, menses, menstrual fluid, as well as other liquid and/or solid waste. By "refastenable" is meant that the absorbent article 10 includes an opening mechanism and an attachment mechanism which will permit the article 10 to be opened and closed at least once. The refastenable absorbent article 10 can be pulled up around the torso of a user just like regular cloth underwear and can be later opened to inspect the interior of the absorbent article 10. Alternatively, the absorbent article 10 can be opened into a flat configuration prior to being placed about the torso of a user and then closed. The attachment mechanism also allows the waist opening of the absorbent article 10 to be snugly adjusted for a more secure fit, if desired.

The method includes the steps of directing or routing a first material 12 from a supply roll 14 through a splitter 16.

The first material 12 can be any natural or synthetic material that has been formed into a woven or non-woven web. The first material 12 can be an elastic material, an elastic laminate, a thermoplastic film, a spunbond web, a bonded carded web, a stretch bonded laminate, etc. Spunbond is a non-woven material that works well in constructing a disposable absorbent article 10. At the splitter 16, the first material 12 is divided or cleaved lengthwise into a first elongated strip 18 and a second elongated strip 20. Alternatively, one can start with two separate materials each wound on a supply roll. In this embodiment, no splitter 16 is required.

A construction adhesive is applied to a surface of the first elongated strip 18 by an adhesive spray unit 22. Similarly, a construction adhesive is applied to a surface of the second elongated strip 20 by an adhesive spray unit 24. Various kinds of hot or cold melt adhesives can be utilized and these are known to those skilled in the art. It should also be noted that the construction adhesive can be applied to only one surface of the first or second elongated strips, 18 or 20 respectively, if desired.

An elastic material 26, in the form of one or more elastic strands, one or more elastic ribbons, an elastic web, etc. is routed from a supply roll 28 toward a nip 30. Desirably, two or more elastic strands 26 are present. More desirably, from between about 3 to about 30 elastic strands are present. Most desirably, from between about 4 to about 20 elastic strands are present. For the purpose of discussion only, the elastic material 26 will be described below as including a plurality of elastic strands 26. The elastic strands 26 can be formed from LYCRA® or from any other elastic material known to those skilled in the art. LYCRA® is a registered trademark of E. I. Du Pont De Nemours & Co. having an office at 1007 Market Street, Wilmington, Del. 19898. The diameter and/or cross-sectional configuration of the elastic strands 26, the decitex (weight in grams per 10,000 meters of a strand) of the elastic strands 26, and the tension imparted into the elastic strands 26 can all be varied to suit one's particular product needs.

At the nip 30, the first elongated strip 18 is positioned over the second elongated strip 20 and the two strips 18 and 20 are aligned. The elastic strands 26 are secured between the first and second elongated strips, 18 and 20 respectively, to form a first elastic laminate 32. The first elastic laminate 32 has a predetermined width ($w_1$). The elastic strands 26 can be spaced apart and aligned parallel to one another. Alternatively, the elastic strands 26 can abut one another, be aligned at an angle to one another or even overlap one another. The elastic strands 26 can be uniformly or randomly arranged relative to one another. The elastic strands 26 can occupy a portion of the surface area of the first elastic laminate 32 or the entire surface area of the first elastic laminate 32. Furthermore, the elastic strands 26 can be located in one or more designated areas of the laminate 32, if desired.

A second material 34 is directed or routed from a supply roll 36 through a splitter 38. The second material 34 can be any natural or synthetic material that has been formed into a woven or non-woven web. The second material 34 can be an elastic material, an elastic laminate, a thermoplastic film, a spunbond web, a bonded carded web, a stretch bonded laminate, etc. Spunbond is a non-woven material that works well in constructing a disposable absorbent article 10. At the splitter 38, the second material 34 is divided or cleaved lengthwise into a first elongated strip 40 and a second elongated strip 42. Alternatively, one can start with two separate materials each wound on a supply roll. In this embodiment, no splitter 38 is required.

A construction adhesive is applied to a surface of the first elongated strip 40 by an adhesive spray unit 44. Similarly, a construction adhesive is applied to a surface of the second elongated strip 42 by an adhesive spray unit 46. Various kinds of hot or cold melt adhesives can be utilized and these are known to those skilled in the art. It should be noted that the construction adhesive can be applied to only one surface of the first or second elongated strips, 40 or 42 respectively, if desired.

An elastic material 48, in the form of one or more elastic strands, one or more elastic ribbons, an elastic web, etc., is routed from a supply roll 50 toward a nip 52. Desirably, two or more elastic strands are present. More desirably, from between about 3 to about 30 elastic strands are present. Most desirably, from between about 4 to about 20 elastic strands are present. For the purpose of discussion only, the elastic material 48 will be described below as including a plurality of elastic strands 48. The elastic strands 48 can be formed from LYCRA® or from any other elastic material known to those skilled in the art. LYCRA® is a registered trademark of E. I. Du Pont De Nemours & Co. having an office at 1007 Market Street, Wilmington, Del. 19898. The diameter and/or cross-sectional configuration of the elastic strands 48, the decitex (weight in grams per 10,000 meters of a strand) of the elastic strands 48, and the tension imparted into the elastic strands 48 can all be varied to suit one's particular product needs.

At the nip 52, the first elongated strip 40 is positioned over the second elongated strip 42 and the two strips 40 and 42 are aligned. The elastic strands 48 are secured between the first and second elongated strips, 40 and 42 respectively, to form a second elastic laminate 54. The second elastic laminate 54 has a predetermined width ($w_2$). The width ($w_2$) of the second elastic laminate 54, can be less than, equal to, or be greater than the width ($w_1$) of the first elastic laminate 32. Desirably, the width ($w_2$) of the second elastic laminate 54 will be approximately equal to the width ($w_1$) of the first elastic laminate 32. The elastic strands 26 can be spaced apart and aligned parallel to one another. Alternatively, the elastic strands 26 can abut one another, be aligned at an angle to one another or even overlap one another. The elastic strands 26 can be uniformly or randomly arranged relative to one another. The elastic strands 26 can occupy a portion of the surface area of the second elastic laminate 54 or the entire surface area of the second elastic laminate 54. Furthermore, the elastic strands 26 can be located in one or more designated areas of the second elastic laminate 54, if desired.

It should be noted that if one or both of the first and second materials, 12 and 34 respectively, is constructed from an elastic material, then there is no need to practice the step of securing elastic strands to form a laminate. For purposes of discussion, the invention will be described below as using the two elastic laminates 32 and 54.

Figure 2:
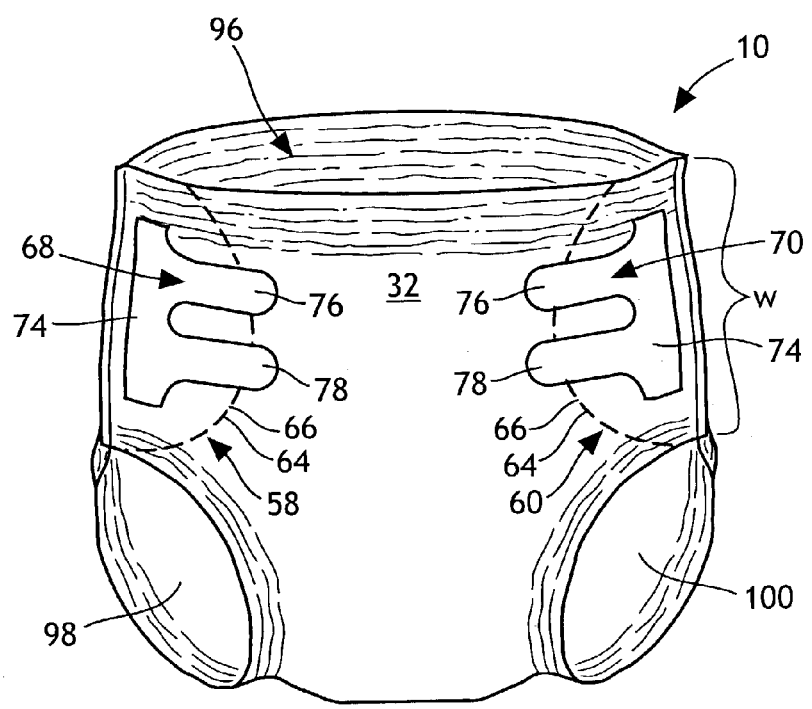
FIG. 2 is a perspective view of a disposable, refastenable absorbent article for absorbing human discharge that includes a pair of lines of perforations aligned non-parallel to a pair of seam lines and further includes a pair of attachment members which bridge over a portion of the pair of lines of perforations.

Referring to FIGS. 1 and 2, the first elastic laminate 32 is directed in a machine direction (MD), moving from left to right in FIG. 1, to a perforation unit 56. The perforation unit 56 is capable of forming at least one line of perforations 58 in a predetermined length 62 of the first elastic laminate 32. Desirably, the perforation unit 56 forms a pair of lines of perforations 58 and 60 in each predetermined length 62 of the first elastic laminate 32. Each of the lines of perforations 58 and 60 extends across the width ($w_1$) of the first elastic laminate 32. Each of the pair of lines of perforations 58 and 60 are tearable by applying a predetermined amount of pressure to either side thereof. The amount of pressure needed to pull the material apart and separate the lines of perforations 58 and 60 should be relatively small. The lines of perforations 58 and 60 can be linear or non-linear on configuration. In FIG. 2, the lines of perforations 58 and 60 have an arcuate configuration, specifically a semi-circular configuration. Desirably, the lines of perforations 58 and 60 can have a unique shape with each being a mirror image of the other. A convex or a concave configuration works well because a large portion of each of the lines of perforations 58 and 60 will be visible in the finished disposable, absorbent article 10.

Figure 3:
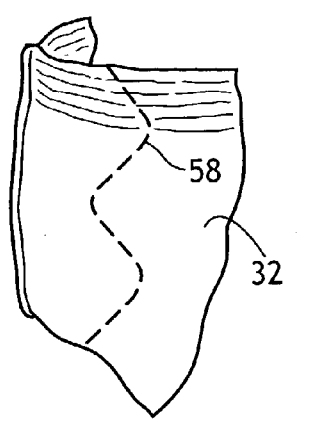
FIG. 3 is a front view of a line of perforations having a sinusoidal configuration and arranged in a non-parallel relationship to the seam line.
Figure 4:
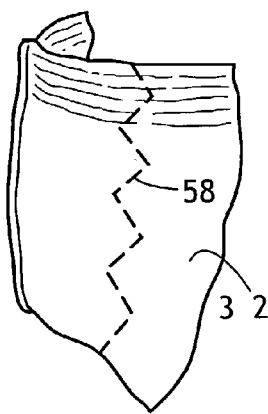
FIG. 4 is a front view of a line of perforations having a herringbone configuration.
Figure 5:
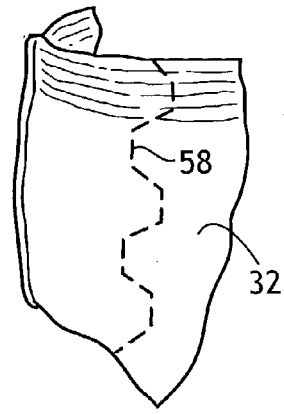
FIG. 5 is a front view of a line of perforations having a saw tooth configuration.

Referring to FIGS. 3–5, three different configurations for the pair of lines of perforations 58 and 60 are depicted. It should be noted that many other configurations can also be used. In FIG. 3, the line of perforations 58 is shown having a sinusoidal configuration. The number of lobes in the sinusoidal pattern can vary to suit one's particular needs. In FIG. 4, the line of perforations 58 is shown having a herringbone configuration. The herringbone configuration is a pattern of oblique parallel lines arranged as single lines alternating in direction. In FIG. 5, the line of perforations 58 is shown having a saw tooth configuration where the lines are arranged in a serrated fashion.

Referring again to FIG. 2, each of the lines of perforations 58 and 60 consist of multiple slits or cuts 64 aligned adjacent to an uncut area 66. The length of each of the slits or cuts 64 can be less than, equal to, or be greater than the length of at least one of the uncut areas 66. The ratio between the length of a slit or cut 64 to an uncut area 66 can be adjusted to increase or decrease the amount of force required to break the lines of perforations 58 and 60. The type of material into which the lines of perforations 58 and 60 are formed, the thickness of the material, the configuration of the lines of perforations 58 and 60, as well as other features, will all have an impact on the amount of force needed to break the lines of perforations 58 and 60. It should also be noted that the amount of force needed to start to break the lines of perforations 58 and 60 may be slightly greater than the amount of force needed to continue to tear open the lines of perforations 58 and 60. Alternatively, a nick or notch, not shown, can be formed at the upper end of each of the lines of perforations 58 and 60 to reduce the amount of force needed to tear open the perforations 58 and 60.

The lines of perforations 58 and 60 can be formed such that each of the slits or cuts 64 has a length that is equal to the length of each of the uncut areas 66. Alternatively, the length of the land and/or slit or cut areas, 64 and 66 respectively, can vary along a portion of or over the total length of each of the lines of perforations 58 and 60. It has been found that when the length of the slits or cuts 64 is greater than the length of the uncut areas 66, that the lines of perforations 58 and 60 can be easily broken. It is important to design the slits or cuts and uncut areas, 64 and 66 respectively, such that the lines of perforations 58 and 60 are easy for the user to break yet are strong enough so as not to break prematurely. Good results have been obtained by dimensioning the length of each of the slits or cuts 64 to be at least two times greater than the length of each of the uncut areas 66. Desirably, the length of each of the slits or cuts 64 will be at least three times greater than the length of each of the uncut areas 66. More desirably, the length of each of the slits or cuts 64 will be at least four times greater than the length of each of the uncut areas 66.

Referring again to FIGS. 1 and 2, the method further includes the step of securing a pair of attachment members 68 and 70 to the first elastic laminate 32 at a bonding station 72. The pair of attachment members 68 and 70 can vary in size, shape, design, number of tabs, etc. As depicted, each of the pair of attachment members 68 and 70 has a base portion 74, a first tab 76 and a second tab 78. The base portion 74 can be secured to the first elastic laminate 32 by an adhesive, by ultrasonics, by a mechanical mechanism, by heat, by pressure, by heat and pressure, by a combination of the aforementioned, or by other means known to those skilled in the art. It should be noted that the base portion 74 can be adhesively attached and then be ultrasonically bonded to provide for a more secure attachment. The base portion 74 is designed to be permanently secured to the first elastic laminate 32 such that it cannot be removed without tearing or destroying the material to which it is secured.

The first and second tabs, 76 and 78 respectively, of each attachment member 68 and 70 are designed to extend over or bridge across one of the pair of lines of perforations 58 or 60. Each of the first and second tabs, 76 and 78 respectively, is removeably attached or secured to the first elastic laminate 32. Each of the first and second tabs, 76 and 78 respectively, can vary in shape, size, dimension, thickness, etc. It should be noted that the shape of the pair of lines of perforations 58 and 60 may dictate how long or narrow each of the tabs 76 and 78 has to be. The first and second tabs, 76 and 78 respectively, are designed to engage and be attached to the first elastic laminate 32, be opened or separated from the first elastic laminate 32 and then be reattached to the first elastic laminate 32 at least once. Desirably, the first and second tabs, 76 and 78 respectively, are designed to be attached to the first elastic laminate 32, be separated or removed from the first elastic laminate 32, and then be reattached to the first elastic laminate 32 at least two times. More desirably, the first and second tabs, 76 and 78 respectively, are designed to be attached to the first elastic laminate 32, be separated from the first elastic laminate 32 and then be reattached to the first elastic laminate 32 several times.

Still referring to FIG. 1, the method also includes the step of positioning and securing an absorbent assembly 80 perpendicularly across the first and second materials, 12 and 34 respectively. In FIG. 1, the first and second materials, 12 and 34 respectively, are the first and second elastic laminates, 32 and 54 respectively. One will notice that the first elastic laminate 32 is aligned approximately parallel to the second laminate 54. Desirably, the first elastic laminate 32 is aligned parallel to and is spaced apart from the second elastic laminate 54. The distance the first elastic laminate 32 is spaced apart from the second elastic laminate 54 can vary depending on the exact size of an absorbent article one desires to manufacture. For example, for a small size absorbent article 10 that may be designed for a baby, the distance between the first and second laminates, 32 and 54 respectively, can be relatively small. In this case, the distance may range from between about 1 inch (about 2.54 centimeters (cm)) to about 6 inches (about 15.2 cm). For a large adult incontinence article, the distance between the first and second laminates, 32 and 54 respectively, can be relatively large. For a large adult incontinence article, the distance may range from between about 4 inches (about 10 centimeters (cm)) to about 20 inches (about 51 cm).

The absorbent assembly 80 can be permanently or temporarily secured to the first and second materials, 12 and 34 respectively, or to the first and second elastic laminates, 32 and 54 respectively, to form a subassembly or chassis 82. The subassembly 82 has a transverse centerline X—X. The subassembly 82 also has a generally H-shaped configuration and some of the material located in the second elastic laminate 54 and even in the absorbent assembly 80, can be cut or formed into a curved or angled section 83. The curved or angled section 83 is formed on each side of the absorbent assembly 80 and serves to provide a good fit around the user's thighs. The curved or angled sections 83 will form a portion of each leg cutout. The absorbent assembly 80 can be secured to the first and second elastic laminates, 32 and 54 respectively, by a construction adhesive, by ultrasonics, by a mechanical mechanism, such as sewing, by a combination of the aforementioned attachment mechanisms or by other means known to those skilled in the art. Desirably, a hot or a cold melt adhesive is used to form a permanent attachment between the absorbent assembly 80 and the first and second materials, 12 and 34 respectively, or between the absorbent assembly 80 and the first and second elastic laminates, 32 and 54 respectively.

Figure 6:
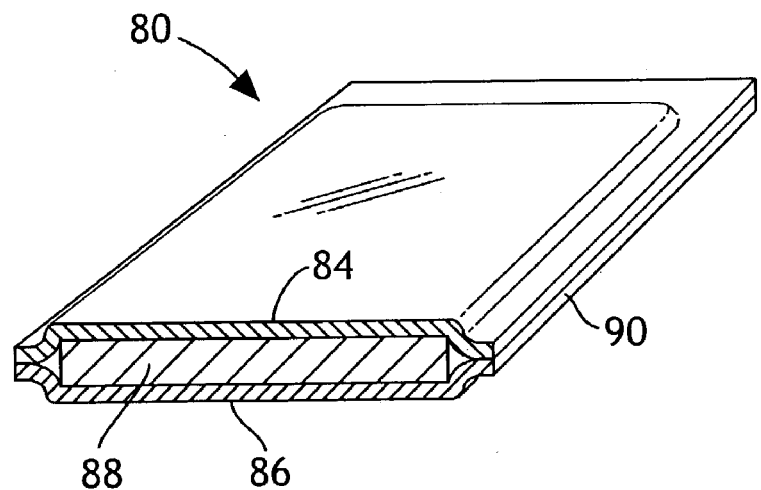
FIG. 6 is a sectioned, perspective view of an absorbent assembly.

Referring now to FIG. 6, a representation of an absorbent assembly 80 is shown. The absorbent assembly 80 includes a liquid permeable bodyside liner 84, a liquid-impermeable backsheet 86 and an absorbent 88 positioned therebetween. One or more layers of absorbent 88 can be present. Furthermore, the absorbent 88 can contain a superabsorbent material, if desired. The liner 84 and the backsheet 86 are joined together to form an outer periphery 90 that completely surrounds and encloses the absorbent 88. The absorbent assembly 80 can then be positioned over a portion of the first and second materials, 12 and 34 respectively, or over a portion of the first and second elastic laminates, 32 and 54 respectively, such that the backsheet 86 contacts and is secured to the first and second elastic laminates, 32 and 54 respectively. A permanent attachment works well but an attachment that allows the absorbent assembly 80 to float or move relative to the first and second laminates 32 and 54 can also be utilized.

Referring again to FIGS. 1 and 2, the method further includes folding the subassembly 82 along the transverse centerline X—X. The first and second elastic laminates 32 and 54 are then bonded together by a first seam line 92 and a second seam line 94. Desirably, the seam lines 92 and 94 are formed by ultrasonic bonds although other bonding methods can be used. Each of the seam lines 92 and 94 is located laterally outward from one of the pair of lines of perforations 58 and 60 to form a waist opening 96 and a pair of leg openings 98 and 100. Desirably, each of the first and second seam lines, 92 and 94 respectively, are aligned non-parallel to one of the pair of lines of perforations 58 and 60. The first and second materials, 12 and 34 respectively, or the first and second elastic laminates, 32 and 54 respectively, are then separated by cut lines 102 and 104. The cut lines 102 and 104 are made at locations laterally outward of the first and second seam lines, 92 and 94 respectively, to form the disposable, refastenable absorbent article 10. The cut lines 102 and 104 can be formed parallel to the first and second seam lines, 92 and 94 respectively. Desirably, the cut lines 102 and 104 are made within about 2 inches (about 5 cm) of the first and second seam lines, 92 and 94 respectively. More desirably, the cut lines 102 and 104 are made within about 1 inch (about 2.5 cm) of the first and second seam lines, 92 and 94 respectively. The cut lines 102 and 104 can be formed by a knife, a die cutter, a water jet, etc. The cut lines 102 and 104 allow for a multiplicity of refastenable absorbent articles 10 to be sequentially formed.

Figure 7:
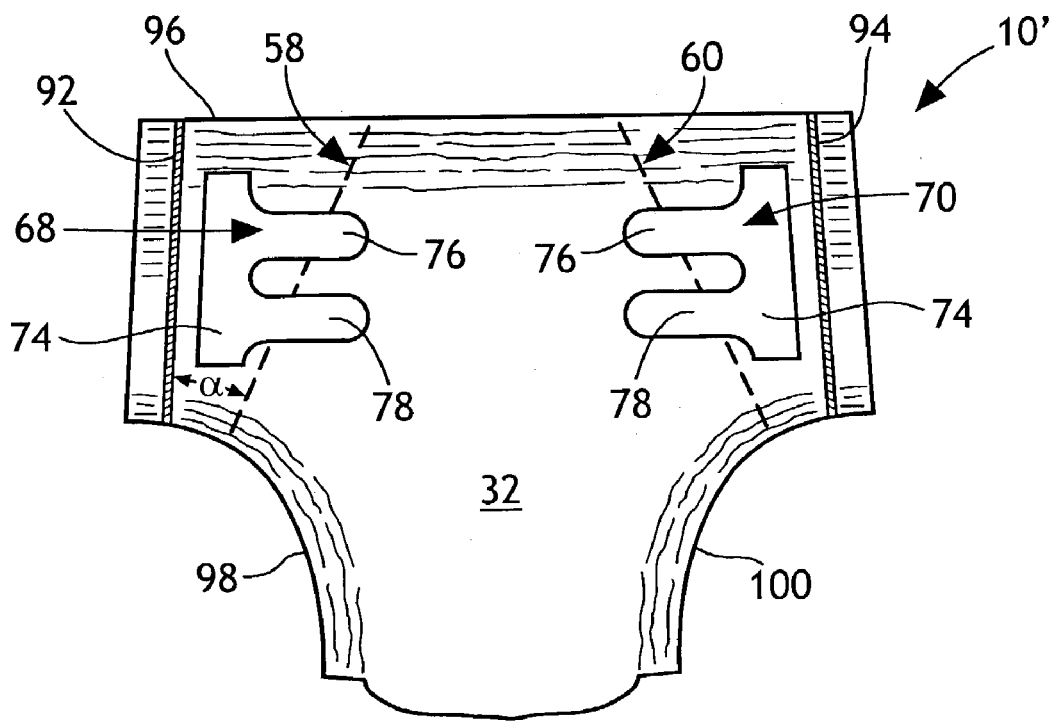
FIG. 7 is a plane view of a disposable, refastenable absorbent article having a pair of linear lines of perforations aligned at an angle so as to be non-parallel to the seam lines.

Referring now to FIG. 7, an alternative embodiment is depicted showing a disposable, refastenable absorbent article 10' having a pair of linear perforation lines 58 and 60. The pair of linear perforation lines 58 and 60 is aligned at an angle to the seam lines 92 and 94. Each of the lines of perforations 58 and 60 taper down and out from the waist opening 96 to one of the leg openings 98 or 100 so as to be aligned non-parallel to one of the adjacent seam lines 92 or 94. Each of the pair of lines of perforations 58 and 60 is aligned at an acute angle a to one of the adjacent seam lines 92 or 94. The angle α can vary from between about 5 degrees to about 60 degrees. Desirably, the angle α can vary from between about 10 degrees to about 45 degrees. More desirably, the angle α can vary from between about 15 degrees to about 35 degrees. At least about 25% of each of the angled lines of perforations 58 and 60 are visible even when partially covered by the tabs 76 and 78 of one of the attachment members 68 and 70. This visibility is important for it will allow the user of the absorbent article 10 or 10' to readily see where the lines of perforations 58 and 60 are located.

When the disposable, refastenable absorbent article 10 or 10' is an incontinent undergarment designed to be worn by older adults who may suffer from poor eye sight, dementia or possibly arthritis, it is best to make them consciously aware of the presence and location of the pair of lines of perforations 58 and 60. This will aid them in being able to tear the lines of perforations 58 and 60. Also, when the user knows that the attachment members 68 and 70 can be released and reapplied both before as well as after the lines of perforations 58 and 60 are broken, it enables the user to keep their disposable absorbent article 10 or 10' snug about their waist at all times.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A method of forming a disposable, refastenable absorbent article, said method comprising the steps of:
    a) directing a first material parallel to and spaced apart from a second material, said first material having a width;
    b) forming a pair of spaced apart lines of perforations across the width of said first material;
    c) securing a pair of attachment members to said first material, each attachment member bridging across one of said pair of lines of perforations and being removeably attached to said first material;
    d) securing an absorbent assembly across said first and second materials to form a subassembly having a transverse centerline;
    e) folding said subassembly on said transverse centerline;
    f) bonding said first and second materials together by first and second seam lines, each of said first and second seam lines being aligned non-parallel to and located outward from one of said pair of lines of perforations to form a waist opening and a pair of leg openings; and
    g) separating said first and second materials at locations outward from each of said first and second seam lines to form a disposable, refastenable absorbent article.

2. The method of claim 1 wherein said first material is elastic.

3. The method of claim 1 wherein said first material is an elastic laminate.

4. The method of claim 1 wherein said second material is elastic.

5. The method of claim 4 wherein said second material is an elastic laminate.

6. The method of claim 1 wherein each of said pair of lines of perforations is non-linear.

7. The method of claim 6 wherein each of said pair of lines of perforations has an arcuate configuration.

8. The method of claim 1 wherein for each of said pair of lines of perforations one line of perforations is a mirror image of said other line of perforations.

9. The method of claim 1 wherein each of said pair of lines of perforations is aligned at an angle to one of said first and second seam lines.

10. A method of forming a disposable, refastenable absorbent article, said method comprising the steps of:
 a) directing a first elastic laminate parallel to and spaced apart from a second elastic laminate, said first laminate having a width;
 b) forming a pair of spaced apart, non-linear lines of perforations across the width of said first laminate;
 c) securing a pair of attachment members to said first laminate, each attachment member bridging across one of said pair of lines of perforations and being removeably attached at one end to said first laminate;
 d) securing an absorbent assembly perpendicularly across said first and second laminates to form a subassembly having a transverse centerline;
 e) folding said subassembly on said transverse centerline;
 f) bonding said first and second laminates together by first and second seam lines, each of said first and second seam lines being aligned laterally outward from one of said pair of lines of perforations to form a waist opening and a pair of leg openings; and
 g) separating said first and second laminates at locations outward from each of said first and second seam lines to form a disposable, refastenable absorbent article.

11. The method of claim 10 wherein each of said pair of lines of perforations is aligned non-parallel to one of said first and second seam lines.

12. The method of claim 10 wherein each of said pair of lines of perforations has an arcuate configuration.

13. The method of claim 10 wherein each of said pair of lines of perforations has a sinusoidal configuration.

14. The method of claim 10 wherein said absorbent assembly includes a liquid permeable bodyside liner, a liquid-impermeable backsheet and an absorbent positioned therebetween, said liner and said backsheet being joined together and said backsheet being secured to both of said first and second laminates.

15. The method of claim 10 wherein each of said pair of lines of perforations is tearable.

16. A method of forming a disposable, refastenable absorbent article comprising the steps of:
 a) splitting a first material into a first elongated strip and a second elongated strip and aligning said first elongated strip over said second elongated strip;
 b) splitting a second material into a first elongated strip and a second elongated strip and aligning said first elongated strip over said second elongated strip;
 c) routing at least one elastic strand between said first and second elongated strips of said first and second materials and securing said at least one elastic strand to said respective first and second elongated strips to form a first laminate and a second laminate, each of said first and second laminates being aligned parallel to one another and being spaced apart, and each of said laminates having a width;
 d) forming a pair of spaced apart, non-linear lines of perforations across the width of said first laminate;
 e) securing a pair of attachment members to said first laminate, each attachment member bridging across one of said pair of lines of perforations and being removeably attached at one end to said first laminate;
 f) securing an absorbent assembly perpendicularly across said first and second laminates to form a subassembly having a transverse centerline;
 g) folding said subassembly on said transverse centerline;
 h) bonding said first and second laminates together by first and second seam lines, each of said first and second seam lines being aligned laterally outward from one of said pair of lines of perforations to form a waist opening and a pair of leg openings; and
 i) separating said first and second laminates at locations laterally outward from each of said first and second seam lines to form a disposable, refastenable absorbent article.

17. The method of claim 16 wherein said subassembly has a generally H-shaped configuration.

18. The method of claim 17 wherein a portion of said generally H-shaped configuration is cut to form leg cutouts.

19. The method of claim 16 wherein a multiplicity of refastenable absorbent articles is sequentially formed by severing each subassembly from an adjacent subassembly.

20. The method of claim 16 wherein said absorbent assembly includes a liquid permeable bodyside liner, a liquid-impermeable backsheet and an absorbent positioned therebetween, said liner and said backsheet being joined together and said backsheet being secured to both of said first and second laminates.

* * * * *